(12) United States Patent
Fantigrossi et al.

(10) Patent No.: US 11,771,441 B2
(45) Date of Patent: Oct. 3, 2023

(54) SPECIFIC DISPOSABLE GUIDE DEVICE FOR SPINAL SURGERY

(71) Applicant: MEDACTA INTERNATIONAL SA, Castel San Pietro (CH)

(72) Inventors: Alfonso Fantigrossi, Castel San Pietro (CH); Francesco Siccardi, Castel San Pietro (CH); Meinrad Fiechter, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 499 days.

(21) Appl. No.: 17/055,643

(22) PCT Filed: May 8, 2019

(86) PCT No.: PCT/IB2019/053765
§ 371 (c)(1),
(2) Date: Nov. 16, 2020

(87) PCT Pub. No.: WO2019/220268
PCT Pub. Date: Nov. 21, 2019

(65) Prior Publication Data
US 2021/0219996 A1     Jul. 22, 2021

(30) Foreign Application Priority Data
May 16, 2018  (IT) .......................... 102018000005435

(51) Int. Cl.
*A61B 17/17*     (2006.01)
*A61B 17/00*     (2006.01)

(52) U.S. Cl.
CPC .. *A61B 17/1757* (2013.01); *A61B 2017/0023* (2013.01)

(58) Field of Classification Search
CPC .................................................. A61B 17/1757
See application file for complete search history.

(56) References Cited

U.S. PATENT DOCUMENTS

| | | | |
|---|---|---|---|
| 5,112,337 A | 5/1992 | Palous et al. | |
| 5,928,232 A | 7/1999 | Howland et al. | |
| (Continued) | | | |

FOREIGN PATENT DOCUMENTS

| | | |
|---|---|---|
| CN | 206560458 | 10/2017 |
| DE | 4219939 A1 | 12/1993 |
| (Continued) | | |

OTHER PUBLICATIONS

International Search Report and Written Opinion for International Application No. PCT/IB2019/053765 dated Aug. 6, 2019.
(Continued)

*Primary Examiner* — Christian A Sevilla
(74) *Attorney, Agent, or Firm* — Meunier Carlin & Curfman LLC

(57) ABSTRACT

Various implementations relate to a guide device for spinal surgery, comprising: two guide sleeves extending between a proximal end and a distal end for guiding a surgical intervention on a vertebra of a patient; a plurality of support elements, wherein each support element defines a contact area specifically configured for abutting against a portion of a virtual surface reproducing the vertebra of the patient, in a coupling configuration; and at least one junction element joining the two guide sleeves together. Each guide sleeve comprises a respective auxiliary sleeve extending between a proximal end and a distal end, and the proximal end of the auxiliary sleeve is located in proximity to the proximal end of the respective guide sleeve.

15 Claims, 8 Drawing Sheets

(56) References Cited

U.S. PATENT DOCUMENTS

| | | | |
|---|---|---|---|
| 8,758,357 B2 | 6/2014 | Frey | |
| 8,870,889 B2 | 10/2014 | Frey | |
| 9,198,678 B2 | 12/2015 | Frey et al. | |
| 9,642,633 B2 | 5/2017 | Frey et al. | |
| 9,987,024 B2 | 6/2018 | Frey et al. | |
| 2002/0123668 A1 | 9/2002 | Ritland | |
| 2007/0066977 A1 | 3/2007 | Assell | |
| 2008/0114370 A1 | 5/2008 | Schoenefeld | |
| 2009/0024132 A1* | 1/2009 | Blain | A61B 17/1728 606/96 |
| 2010/0023018 A1* | 1/2010 | Theofilos | A61B 17/1757 606/96 |
| 2011/0319745 A1 | 12/2011 | Frey | |
| 2012/0130382 A1 | 5/2012 | Iannotti et al. | |
| 2012/0245587 A1 | 9/2012 | Fang et al. | |
| 2013/0053854 A1 | 2/2013 | Schoenefeld | |
| 2013/0123850 A1* | 5/2013 | Schoenefeld | A61B 17/7055 606/248 |
| 2013/0218163 A1 | 8/2013 | Frey | |
| 2014/0074099 A1 | 3/2014 | Vigneron et al. | |
| 2014/0200618 A1* | 7/2014 | Donner | A61F 2/4611 606/281 |
| 2014/0277460 A1* | 9/2014 | Schifano | A61B 17/1757 606/86 R |
| 2014/0358152 A1 | 12/2014 | Condino et al. | |
| 2016/0030067 A1* | 2/2016 | Frey | A61B 50/33 606/86 A |
| 2018/0042619 A1 | 2/2018 | Frey et al. | |
| 2018/0177512 A1 | 6/2018 | Hogan et al. | |
| 2018/0296254 A1* | 10/2018 | Tsai | A61B 17/7032 |
| 2021/0077119 A1 | 3/2021 | Siccardi et al. | |

FOREIGN PATENT DOCUMENTS

| | | | |
|---|---|---|---|
| DE | 102016218965 | | 4/2018 |
| EP | 2502582 A1 | | 9/2012 |
| EP | 2749235 A1 | | 7/2014 |
| JP | 2015208566 | | 11/2015 |
| JP | 2016524506 A | | 8/2016 |
| TW | 200908927 A | | 3/2009 |
| TW | 201238556 A | | 10/2012 |
| WO | 9600049 A1 | | 1/1996 |
| WO | 2012156466 | | 11/2012 |
| WO | 2013158521 A1 | | 10/2013 |
| WO | 2014070889 A1 | | 5/2014 |
| WO | 2014090908 A1 | | 6/2014 |
| WO | WO-2014090908 A1 * | 6/2014 | A61B 17/1757 |
| WO | 2014197844 A1 | | 12/2014 |
| WO | 2016075581 A1 | | 5/2016 |
| WO | 2016075660 A1 | | 5/2016 |
| WO | 2018055494 A1 | | 3/2018 |
| WO | 2018055518 A1 | | 3/2018 |

OTHER PUBLICATIONS

Radermacher, Klaus, Computer Assisted Orthopaedic Surgery with Individual Templates, Helmholtz-Institute for Biomedical Engineering, 2 pages, 1997.

Berry et al., Personalised image-based templates for intra-operative guidance, Proceedings of the Institution of Mechanical Engineers, Part H: Journal of Engineering in Medicine, vol. 219, pp. 111-118, 2004.

Lu et al., A Novel Patient-Specific Navigational Template for Cervical Pedicle Screw Placement. SPINE, vol. 34, No. 26, pp. E959-E964, 2009.

Popescu et al., Design and Rapid Manufacturing of Patient-Specific Spinal Surgical Guides: A Survey, Proceedings in Manufacturing Systems, vol. 7, Issue 2, pp. 115-120, 2012.

Lu et al., A novel computer-assisted drill guide template for placement of C2 laminar screws, Eur Spine J, vol. 18, pp. 1379-1385, 2009.

Lu et al., Rapid prototyping drill guide template for lumbar pedicle screw placement, Chinese Journal of Traumatology, vol. 12(3), pp. 171-177, 2009.

Ryken et al., Image-based drill templates for cervical pedicle screw placement, J Neurosurg Spine vol. 10, pp. 21-26, 2009.

Brussel et al., Medical Image-Based Design of an Individualized Surgical Guide for Pedicle Screw Insertion, 18th Annual International Conference of the IEEE Engineering in Medicine and Biology Society, Amsterdam, pp. 225-226, 1996.

International Search Report and Written Opinion, issued by the International Searching Authority (ISAEP) in Application No. PCT/IB2018/060161 dated Apr. 5, 2019. 9 pages.

International Search Report and Written Opinion, issued by the International Searching Authority (ISAEP) in Application No. PCT/IB2019/060161 dated Apr. 2, 2020. 11 pages.

International Search Report and Written Opinion, issued by the International Searching Authority (ISAEP) in Application No. PCT/IB2018/060160 dated Apr. 5, 2019. 13 pages.

Office Action issued for U.S. Appl. No. 16/956,253, dated Oct. 12, 2021.

Office Action issued for U.S. Appl. No. 17/281,900 dated Dec. 2, 2021.

International Search Report and Written Opinion issued for Application No. PCT/IB2017/055688, dated Nov. 16, 2017, 11 pages.

English Translation of Notice of Reasons of Refusal in JP 2019-536354, dated Feb. 10, 2020, 7 pages.

International Search Report and Written Opinion issued for Application No. PCT/IB2017/055588, dated Nov. 22, 2017, 13 pages.

International Search Report and Written Opinion for International Application No. PCT/IB2019/058162, dated Jan. 22, 2020, 16 pages.

English Translation of Notice of Reasons of Refusal in JP 2019-536348, dated Feb. 27, 2020, 14 pages.

Office Action issued for U.S. Appl. No. 16/333,057, dated Jul. 30, 2020.

Office Action issued for U.S. Appl. No. 16/333,055, dated Dec. 8, 2020.

Notice of Allowance received in connection with U.S. Appl. No. 16/956,253, dated Feb. 8, 2022, 10 pages.

Non-Final Office Action received in connection with U.S. Appl. No. 17/357,612, dated Nov. 2, 2022, 27 pages.

* cited by examiner

SPECIFIC DISPOSABLE GUIDE DEVICE FOR SPINAL SURGERY

The present invention relates to the technical field of spinal surgery, more specifically it relates to a specific disposable guide device for spinal surgery. This device is used to help the surgeon in the drilling of a vertebra.

Vertebral drilling is often required in the field of spinal surgery, for example for inserting a Kirschner wire, for inserting a guide wire for the application of cannulated screws, or still for inserting solid screws. The drilling direction must be defined with great precision because the hole, which originates on the lamina, must often proceed along a very precise direction, for example along the pedicle of the vertebra. Because of the critical nature of the drilling operation, several solutions have been developed to assist the surgeon.

First of all, techniques have been developed which, through the methods commonly used in diagnostic imaging (for example, computerized tomography), allow digital reconstruction of the specific anatomy of the individual vertebra of the individual patient that must undergo surgery.

The digital model of the individual vertebra allows a physical model to be obtained, on which the drilling is already preoperatively planned in the finest details.

Finally, starting from the vertebra model and the drilling direction deemed optimal by the surgeon, it is possible to construct specific disposable guide devices for drilling. The adjective "specific" as used herein and hereinafter means that the guide device has been customized, or shaped so as to adapt to the anatomy of a specific vertebra of a specific patient.

In this field, guide devices are mainly employed to help the surgeon during pedicle screw insertion, so that the screw can be inserted according to a pre-planned optimal axis of the screw.

However, these devices may be used in spinal surgery for other purposes; for instance, as cutting guides during PSO (pedicle subtraction osteotomies), laminotomy or facetectomies.

In general, guide devices are provided with one or more guide sleeves and one or more contact elements adapted to mate with the vertebrae of the patient in a stable and well-defined configuration.

Guide sleeves define the direction of advancement of the surgical tool. As the skilled person can well understand, in order to faithfully maintain the optimal direction defined during the preoperative phase, the device must absolutely be able to be firmly rested on the vertebra and have a single well-defined position of use easily obtainable in the real operating field.

In order to achieve this goal, a firm contact between the guide device and the patient's bone structure is required.

For optimal positioning of the guide, the surgeon must wash the surrounding tissue away from a large area of the bone, and in some cases cut the ligaments. This operation often proves to be difficult and costly in terms of time and can lead to complications and lengthening of the patient's hospitalization.

Furthermore, the remaining tissue that the surgeon is unable to remove and the surface of the bone itself can lead to slipping and deviation of both the guide device and the tool used for drilling.

If this were to happen, the pedicle screws or bone resections would be positioned incorrectly or sub-optimally.

As mentioned above, the orientation with which the surgical tool reaches the surface of the vertebra, to perforate it, is defined by the optimal direction the drilling must have with respect to the vertebra. For this reason, the tool may have to reach the surface of the vertebra with a strong inclination that favours undesired displacement thereof, also due to the slippery surface of the vertebra. In this case, therefore, despite the care taken in planning the surgical operation and constructing the guide device, the drilling of the vertebra may be suboptimal.

In view of the foregoing, the technical problem underlying the present invention is to provide a disposable guide device for spinal surgery, which allows the slipping issues on the patient's vertebra to be minimized or prevented.

The aforementioned technical problem is solved by means of a guide device for spinal surgery, according to claim 1.

More particularly, the aforementioned technical problem is solved by means of a device comprising:

two guide sleeves extending between a proximal end and a distal end for guiding a surgical intervention on a vertebra of a patient;

a plurality of support elements, wherein each support element defines a contact area specifically configured for abutting against a portion of a virtual surface reproducing the vertebra of the patient, in a coupling configuration; and at least one junction element joining the two guide sleeves together.

Furthermore, each guide sleeve comprises a respective auxiliary sleeve extending between a proximal end and a distal end, and the proximal end of the auxiliary sleeve is located in proximity to the proximal end of the respective guide sleeve.

Advantageously, each guide sleeve and the corresponding auxiliary sleeve have a diverging development starting from the respective proximal ends.

Preferably, each guide sleeve extends along a respective main axis and the respective auxiliary sleeve extends along a respective auxiliary axis. Advantageously, each auxiliary axis intersects the respective main axis.

In accordance with some embodiments of the guide device, each auxiliary axis forms an angle $\alpha$ with the respective main axis. Preferably, the angle $\alpha$ formed by an auxiliary axis and the respective main axis is comprised between 20° and 60°, even more preferably between 25° and 45°.

An insertion duct is located within each guide sleeve and a service duct is located within each auxiliary sleeve.

In some embodiments, the proximal opening of the service duct is defined in the wall of the insertion duct, near its proximal end.

In some embodiments, the proximal opening of the service duct is slightly spaced apart from the proximal opening of the insertion duct.

Both the insertion ducts and the service ducts define respective insertion axes for a surgical tool whose use is preferably planned in detail in the preoperative phase.

The diameter of the insertion duct is such as to allow the insertion of a main surgical tool. Said diameter can be selected from 3-18 mm, 3-12 mm, 3-9 mm, 3-6 mm.

The diameter of the service duct is such as to allow the insertion of a preparatory drill. Said diameter can be selected from 1.8-4 mm, 2-3 mm.

Advantageously, the auxiliary axis reaches the minimum distance from the main axis in proximity to the virtual surface of the vertebra.

Preferably, the auxiliary axis intersects the main axis in proximity to the virtual surface of the vertebra.

Preferably, the auxiliary axis reaches the minimum distance from the main axis or intersects it, at a point inside the vertebra, within 5 mm from the virtual surface.

Advantageously, the guide sleeves can be oriented so that the proximal ends are more distant from each other with respect to the distal ends.

Preferably, each auxiliary axis forms an angle β with the portion of the virtual surface of the vertebra on which it is incident, the angle β being favourable to the use of the preparatory drill.

The angle β is preferably comprised between 60° and 120°, even more preferably between 75° and 105°.

Preferably, the at least one junction element extends transversely to the two guide sleeves to place them in rigid connection with one another. More preferably, the junction element is located in proximity to the distal end of the guide sleeves.

Preferably, the guide sleeves are spaced apart from each other by a distance at least suitable to allow the housing of a spinous process of the vertebra to be operated on.

Preferably, the junction element takes an inverted "U" shape that defines therein a seat for housing the spinous process of the vertebra.

In some embodiments, the seat for housing the spinous process is open in the craniocaudal direction.

Alternatively, the seat for housing the spinous process can be closed in the craniocaudal direction by one or two partitions connecting the sides of the junction element.

Preferably, the junction element comprises a handle suitable to facilitate the surgeon's handling of the device.

Preferably, the support elements, and in particular the respective contact areas, are designed in a patient-specific manner during the preoperative phase.

Preferably, at least one of the support elements is shaped like a hook, so as to at least partially encircle a portion of the vertebra.

Preferably, each guide sleeve is provided with a further own contact portion, near the proximal end, configured for abutting against a portion of the virtual surface of the vertebra.

Further features and advantages of the patient-specific disposable guide device according to the invention will become more apparent from the description, provided hereinafter, of a number of embodiments described by way of non-limiting example with reference to the accompanying drawings, wherein.

Figure 1:
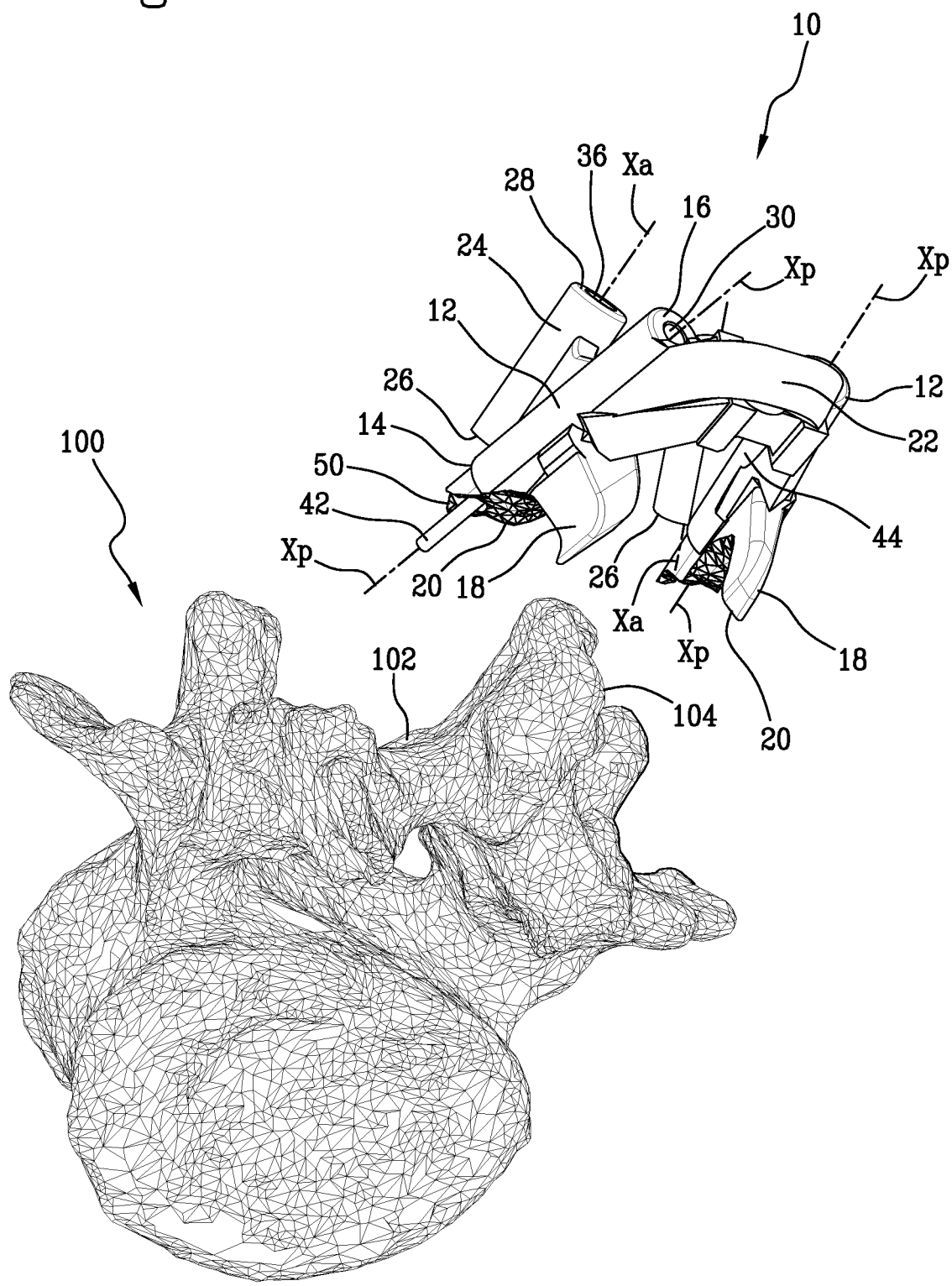
FIG. 1 is a perspective view of a disposable guide device according to a first embodiment of the invention.

With reference to the accompanying figures, the numeral 10 indicates a guide device for spinal surgery according to the present invention.

In particular, the figures show the device 10 approached to a specific vertebra 100 for which it was designed and constructed.

The disposable guide device 10 for spinal surgery comprises:
- two guide sleeves 12 extending between a proximal end 14 and a distal end 16 for guiding a surgical intervention on a vertebra 100 of a patient;
- a plurality of support elements 18, wherein each support element 18 defines a contact area 20 specifically configured for abutting against a portion of a virtual surface 102 reproducing the vertebra 100 of the patient, in a coupling configuration; and
- at least one junction element 22 joining the two guide sleeves 12 together.

In the disposable guide device 10 according to the invention, each guide sleeve 12 comprises a respective auxiliary sleeve 24 extending between a proximal end 26 and a distal end 28, and the proximal end 26 of the auxiliary sleeve 24 is located in proximity to the proximal end 14 of the respective guide sleeve 12.

Reference is made herein and hereinafter to a virtual surface 102 reproducing the vertebra 100 of the patient. As known per se, this virtual surface 102 is obtained from the three-dimensional model of the patient's vertebra 100. A specific virtual surface 102 is therefore uniquely identified for each individual guide device 10. Moreover, when the guide device 10 is correctly arranged in the coupling configuration, its position is uniquely defined with respect to the virtual surface 102. Due to the uniqueness of the virtual surface 102 and the uniqueness of the reciprocal position between the same and the guide device 10 in the coupling configuration, some features of the guide device 10 can be defined unambiguously in relation to the virtual surface 102. In the present discussion, the expressions "in use", "during use" or the like refer to the guide device 10 in the configuration of coupling to the virtual surface 102.

Since the virtual surface 102 faithfully reproduces the vertebra 100, in the attached figures it is represented as resting on the vertebra 100 itself and can actually be identified as the real surface of the vertebra 100, without however introducing ambiguities or errors.

Advantageously, each guide sleeve 12 and the corresponding auxiliary sleeve 24 have a diverging development starting from the respective proximal ends 14, 26.

Preferably, each guide sleeve 12 extends along a respective main axis Xp and the respective auxiliary sleeve 24 extends along a respective auxiliary axis Xa. In this case, advantageously, each auxiliary axis Xa intersects the respective main axis Xp.

In accordance with some embodiments of the guide device 10, each auxiliary axis Xa forms an angle α with the respective main axis Xp.

Preferably, the angle α formed by an auxiliary axis Xa and the respective main axis Xp is comprised between 20° and 60°, even more preferably between 25° and 45°.

If the main axis Xp and the secondary axis intersect, they lie in the same plane and the angle α is immediately identifiable by the skilled person. Vice versa, if there is no plane containing both the main axis Xp and the auxiliary axis Xa (i.e. in the case where these axes are skew), it is possible, for example, to consider by analogy the angle formed by the projections of the axes on a plane perpendicular to the segment that represents the minimum distance between the two axes.

Note that the terms "distal" and "proximal", as used herein, refer to the relative position of an element (e.g. the end of a sleeve) with respect to the virtual surface 102 of the vertebra 100.

Each guide sleeve 12 houses an insertion duct 30 extending with substantial continuity between the distal end 16 and the proximal end 14. In other words, the insertion duct 30 extends between a distal opening 32, formed in the distal end 16 of the guide sleeve 12, and a proximal opening 34, formed in the proximal end 14 of the guide sleeve 12.

Similarly, each auxiliary sleeve 24 houses a service duct 36 extending with substantial continuity between the distal end 28 and the proximal end 26. In other words, the service duct 36 extends between a distal opening 38, formed in the distal end 28 of the auxiliary sleeve 24, and a proximal opening 40, formed in the proximal end 26 of the auxiliary sleeve 24.

In accordance with some embodiments (see, for example, FIGS. 6-8), the proximal opening 40 of the service duct 36 is defined in the wall of the insertion duct 30, near its proximal end 14. In these embodiments, the service duct 36 opens into the insertion duct 30.

In other embodiments (see, for example, FIGS. 1-5), the proximal opening 40 of the service duct 36 is slightly spaced apart from the proximal opening 34 of the insertion duct 30.

Both the insertion ducts 30 and the service ducts 36 define respective insertion axes for a tool whose use is preferably planned in detail in the preoperative phase.

Therefore, in each duct 30, 36, the distal opening 32, 38 corresponds to an access opening of a tool, while the proximal opening 34, 40 faces the patient's vertebra 100, in the vicinity of the same.

Figure 2:
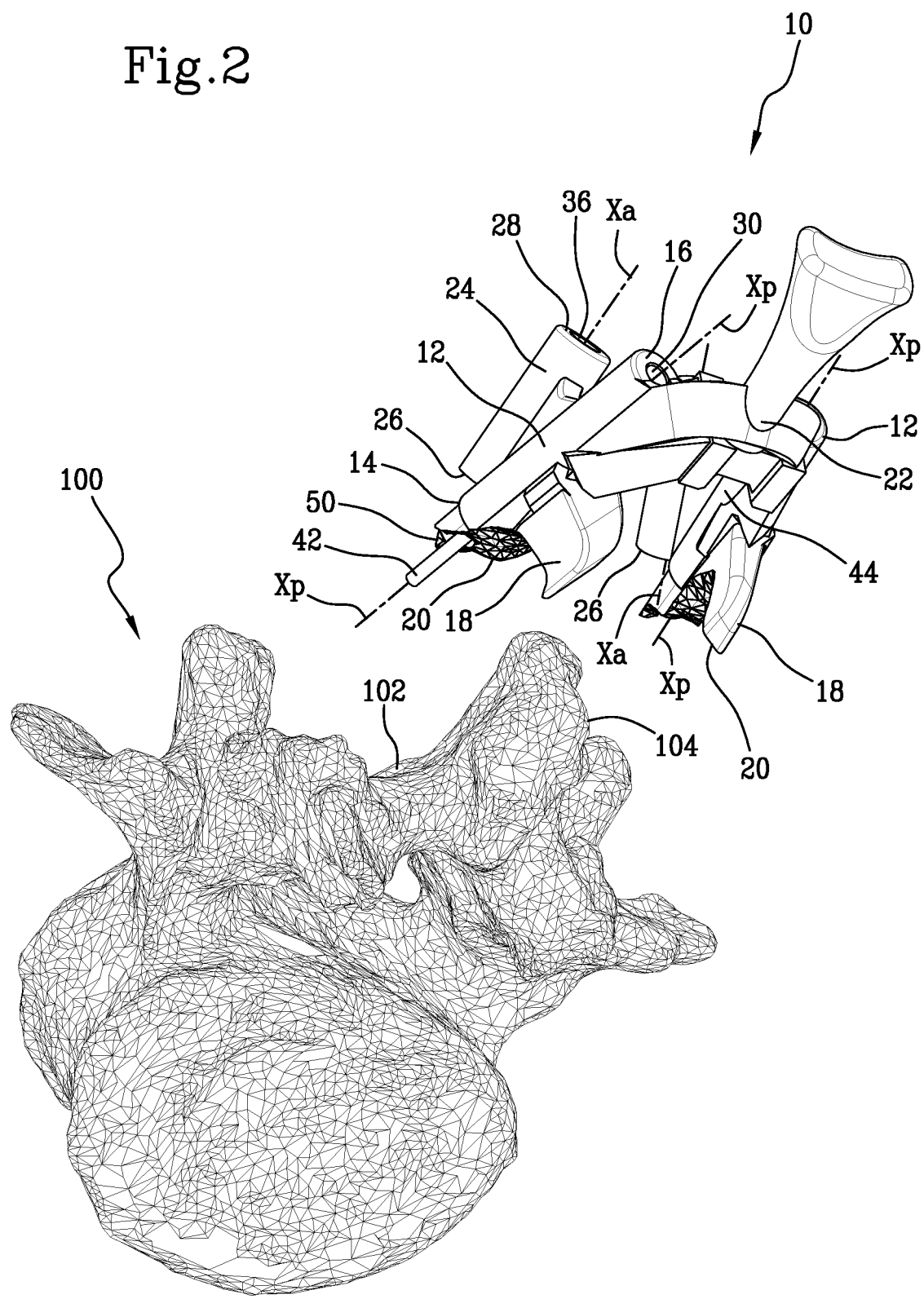
FIG. 2 is a perspective view of a disposable guide device according to a second embodiment of the invention when it is approached to the respective vertebra.
Figure 3:
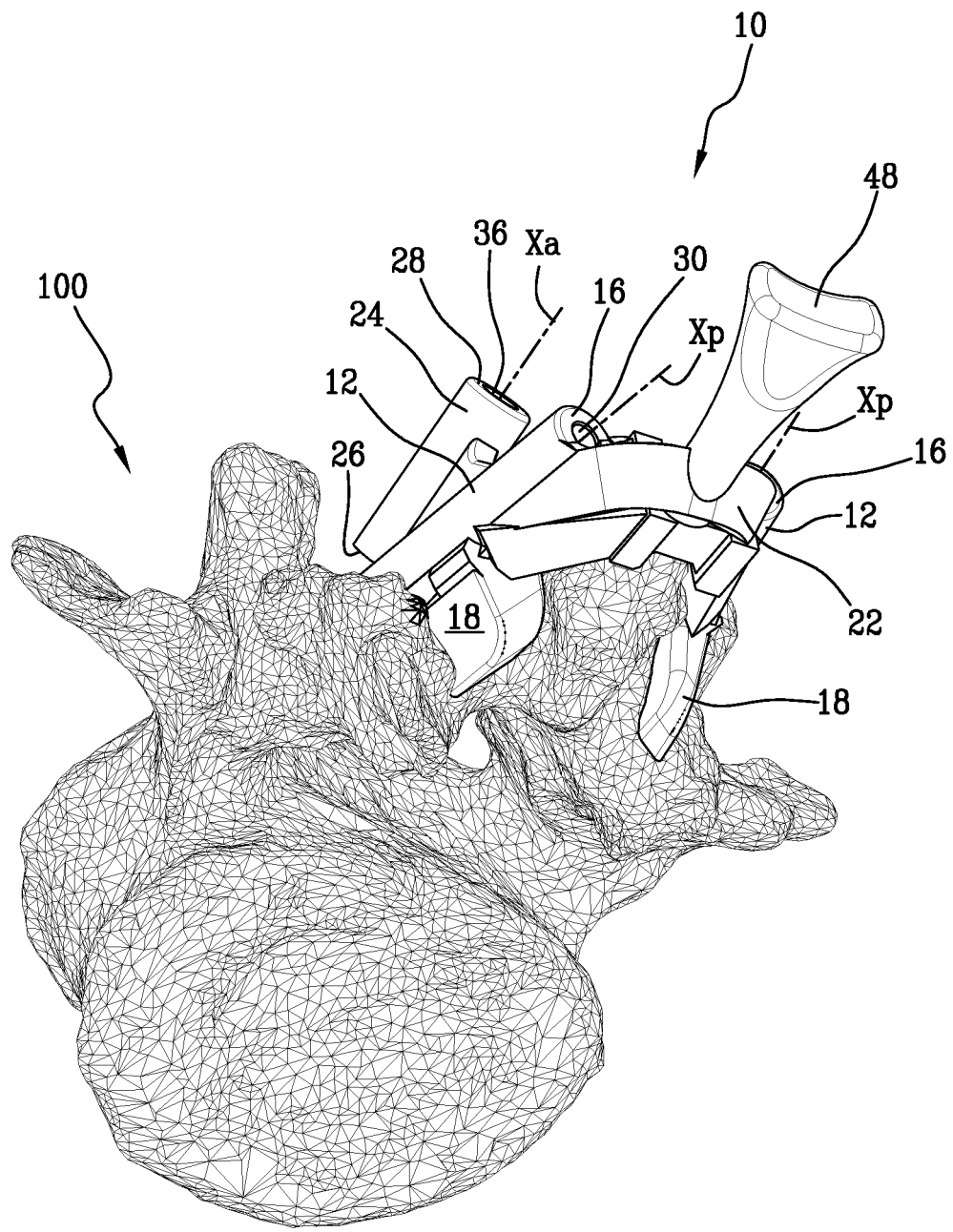
FIG. 3 shows a view similar to that of FIG. 2 in which the guide device is correctly resting on the respective vertebra.
Figure 4:
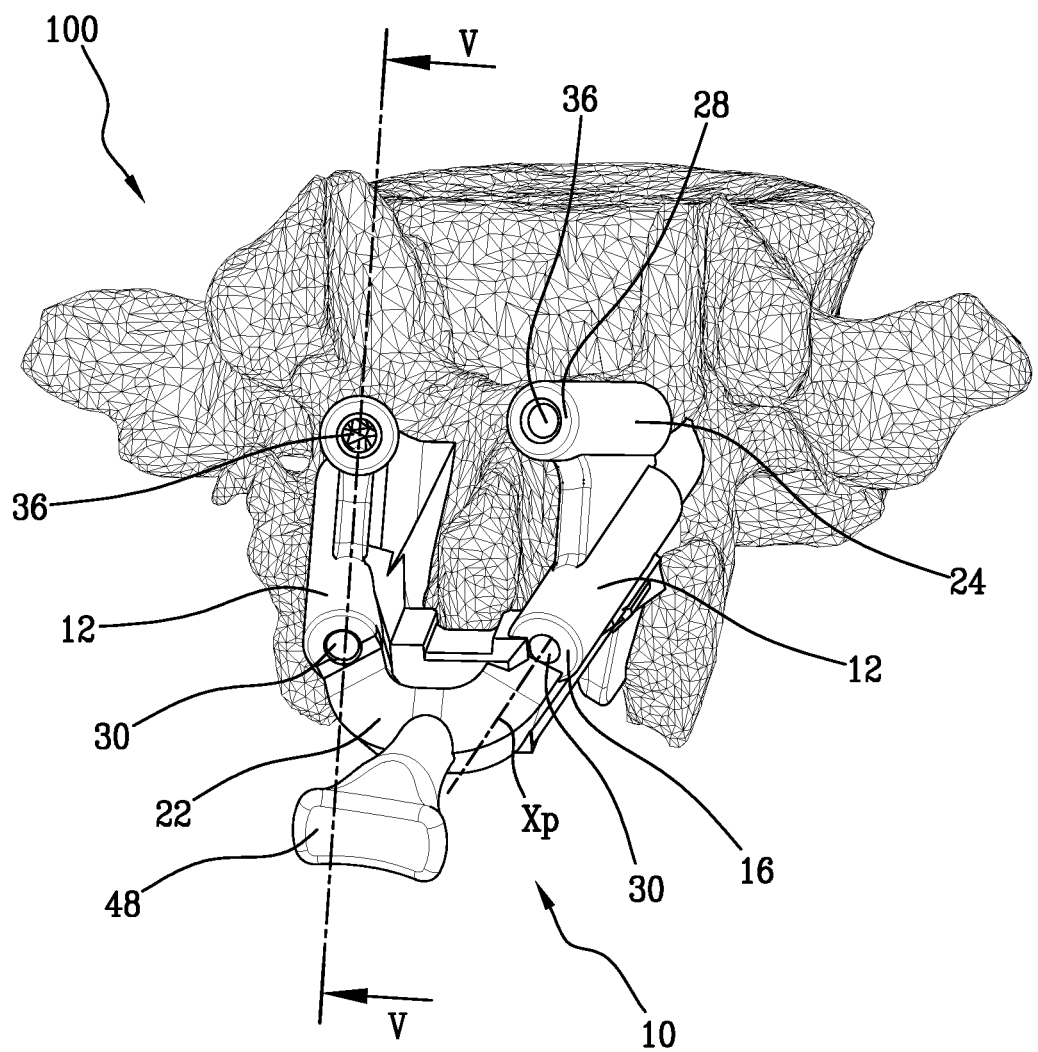
FIG. 4 shows a different view of the device of FIG. 2 correctly resting on the respective vertebra.
Figure 5:
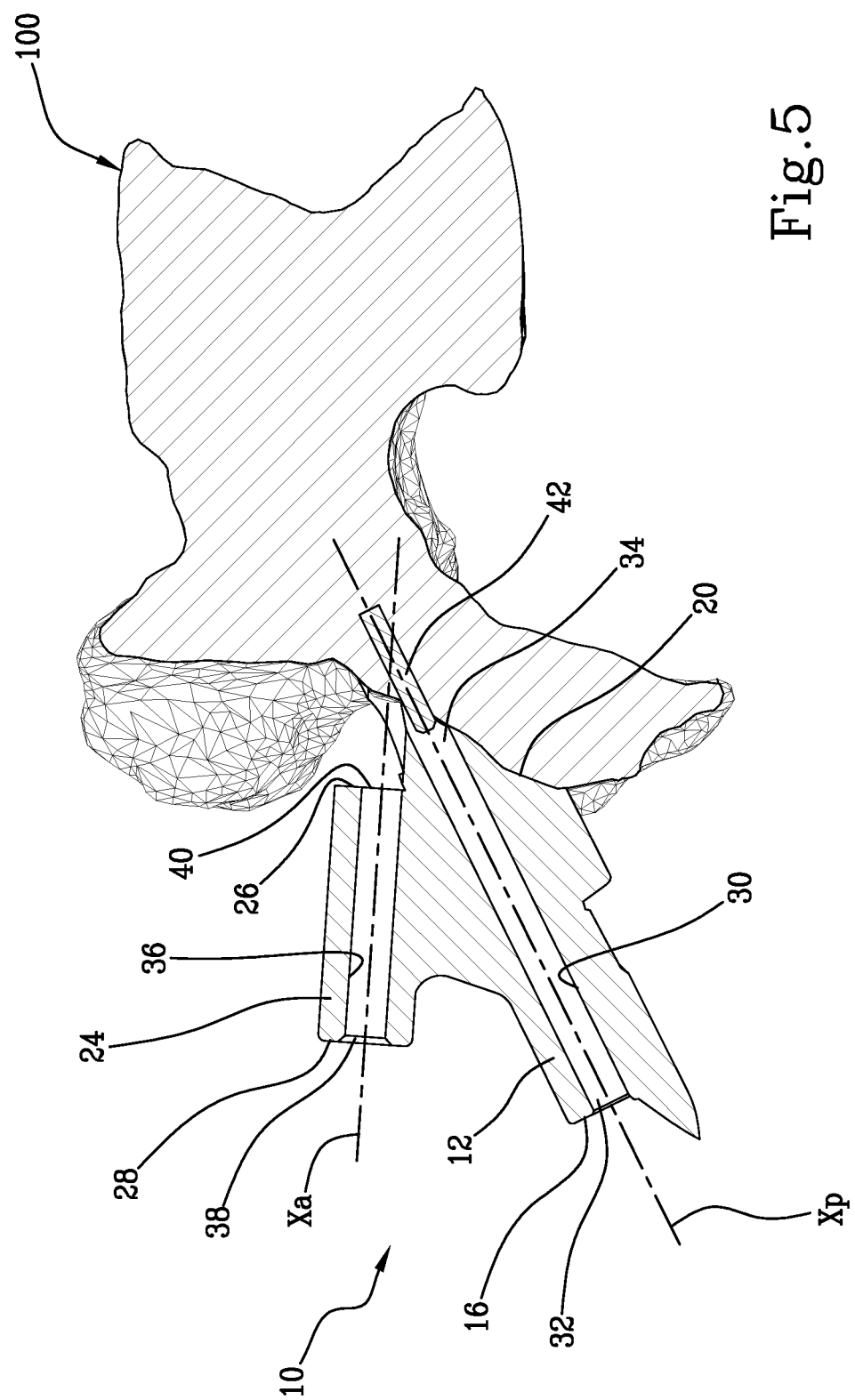
FIG. 5 shows a cross section made along the line V-V in FIG. 4.

Tools that can be used with the guide device 10 can typically be: a Kirschner wire, a cannulated polyaxial screw, a solid polyaxial screw, a drill, a tapper, a punch, a probe, a marker, a pin. These tools are referred to hereinafter as the "main surgical tools" since it is these that carry out the main phase of the surgical intervention. A main surgical tool 42 is schematically represented in FIGS. 1, 2 and 5.

In a known manner, therefore, the diameter of the insertion duct 30 is such that it allows the insertion of a main surgical tool 42. Depending on the areas of application, the inner diameter of the insertion ducts can be selected from 3-18 mm, 3-12 mm, 3-9 mm, 3-6 mm.

In accordance with the invention, the diameter of the service duct 36 is such that it allows the insertion of a preparatory drill. Depending on the areas of application, the inner diameter of the insertion ducts can be selected from 1.8-4 mm, 2-3 mm. Such a preparatory drill has the task of superficially incising the bone to facilitate the use of the main surgical tool 42.

In light of the above, the skilled person can readily understand that the main axis Xp of the guide sleeve 12 defines the direction of advancement of the insertion duct 30, hence of the main surgical tool 42. Similarly, the auxiliary axis Xa of the auxiliary sleeve 24 defines the direction of advancement of the service duct 36, hence of the preparatory drill (not shown in the figures). The direction of advancement Xa of the preparatory drill can be advantageously defined during the preoperative planning, most of all to optimally define the angle β at which the preparatory drill approaches the virtual surface 102 of the vertebra 100. Some considerations on the angle β are given below.

Advantageously, therefore, the auxiliary axis Xa reaches the minimum distance from the main axis Xp in proximity to the virtual surface 102 of the vertebra 100. Preferably, the auxiliary axis Xa intersects the main axis Xp in proximity to the virtual surface 102 of the vertebra 100.

Figure 8:
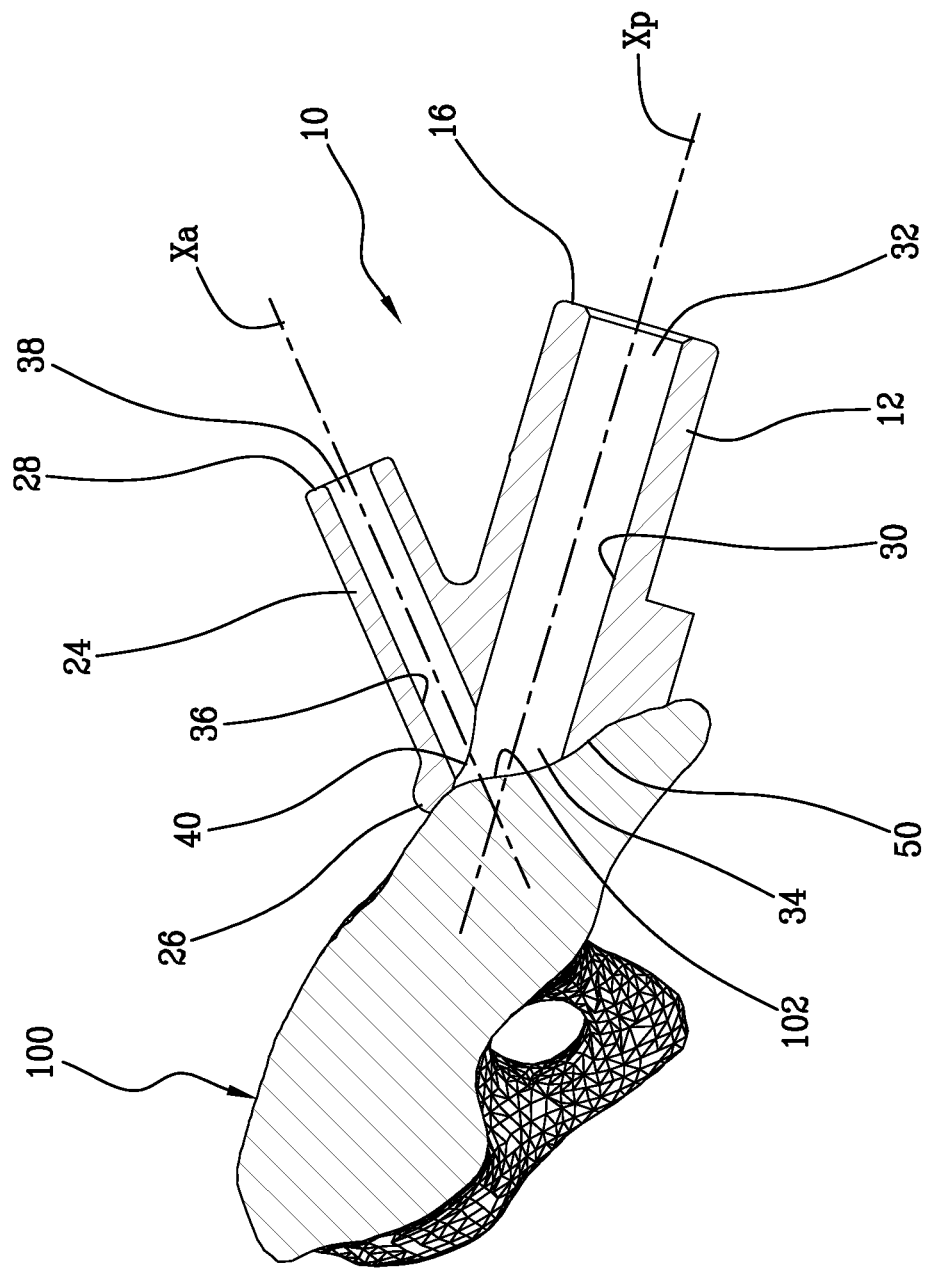
FIG. 8 shows a cross section made along the line VIII-VIII in FIG. 7.

Preferably, as can be seen in the cross sections depicted in FIGS. 5 and 8, the auxiliary axis Xa reaches the minimum distance from the main axis Xp or intersects it, at a point inside the vertebra 100. In accordance with some embodiments, the auxiliary axis Xa reaches the minimum distance from the main axis Xp or intersects it within 5 mm from the virtual surface 102.

According to an optional aspect of the present invention, the guide sleeves 12 can be oriented so that the proximal ends 14 are more distant from each other with respect to the distal ends 16. In other words, the main axes Xp of the guide sleeves 12 are oriented, starting from the respective distal ends 16, away from each other. Therefore, the guide device 10 according to the present invention preferably has a "diverging" configuration, in which the guide sleeves 12 diverge in the proximal region. Advantageously, this simplifies the positioning of the device 10, thus reducing the space required for insertion by the surgeon.

As the skilled person can well understand, the orientation of each auxiliary sleeve 24 can be chosen rather freely during the design of the device 10. In particular, the orientation with respect to the virtual surface 102 of the vertebra 100 can be defined regardless of the direction Xp to be followed by the main surgical tool 42.

The orientation and positioning of the guide sleeves 12 and the respective auxiliary sleeves 24 are designed during the preoperative phase, by means of computer-aided design tools, on a three-dimensional model of the bone structure. This model is developed from a three-dimensional image obtained, for example, by computerized tomography and/or magnetic resonance of the patient's vertebra 100. Therefore, each sleeve 12, 24 is designed so as to uniquely define the direction of the respective axis Xp, Xa with respect to the vertebra 100.

Preferably, the device 10 is constructed so that each auxiliary axis Xa, in use, forms an angle @ with the portion of the virtual surface 102 of the vertebra 100 on which it is incident, the angle β being favourable to the use of the preparatory drill. The angle @ formed, in use, by each auxiliary axis Xa with the portion of the virtual surface 102 of the vertebra 100 on which it is incident is preferably comprised between 60° and 120°, even more preferably between 75° and 105°.

As mentioned previously, a junction element 22 is provided between the two guide sleeves 12.

Preferably, the at least one junction element 22 extends transversely to the two guide sleeves 12 to place them in rigid connection with one another. More preferably, the junction element 22 is located in proximity to the distal end 16 of the guide sleeves 12.

Therefore, such a junction element 22 is a preferably non-straight crosspiece extending between the two guide sleeves 12 to space them apart and keep them firmly in a pre-established mutual position.

Preferably, the guide sleeves 12 are spaced apart from each other by a distance at least suitable to allow the housing of a spinous process 104 of the vertebra 100 to be operated on.

In accordance with some embodiments, the junction element 22 takes an inverted "U" shape that defines therein a seat 44 for housing the spinous process 104 of the vertebra 100.

According to some embodiments, for example those shown in FIGS. 1-4, the seat 44 for housing the spinous process 104 is open in the cranial-caudal direction in order to prevent the patient's ligaments from having to be excised before placing the guide device 10 in the coupling configuration (open profile).

Figure 6:
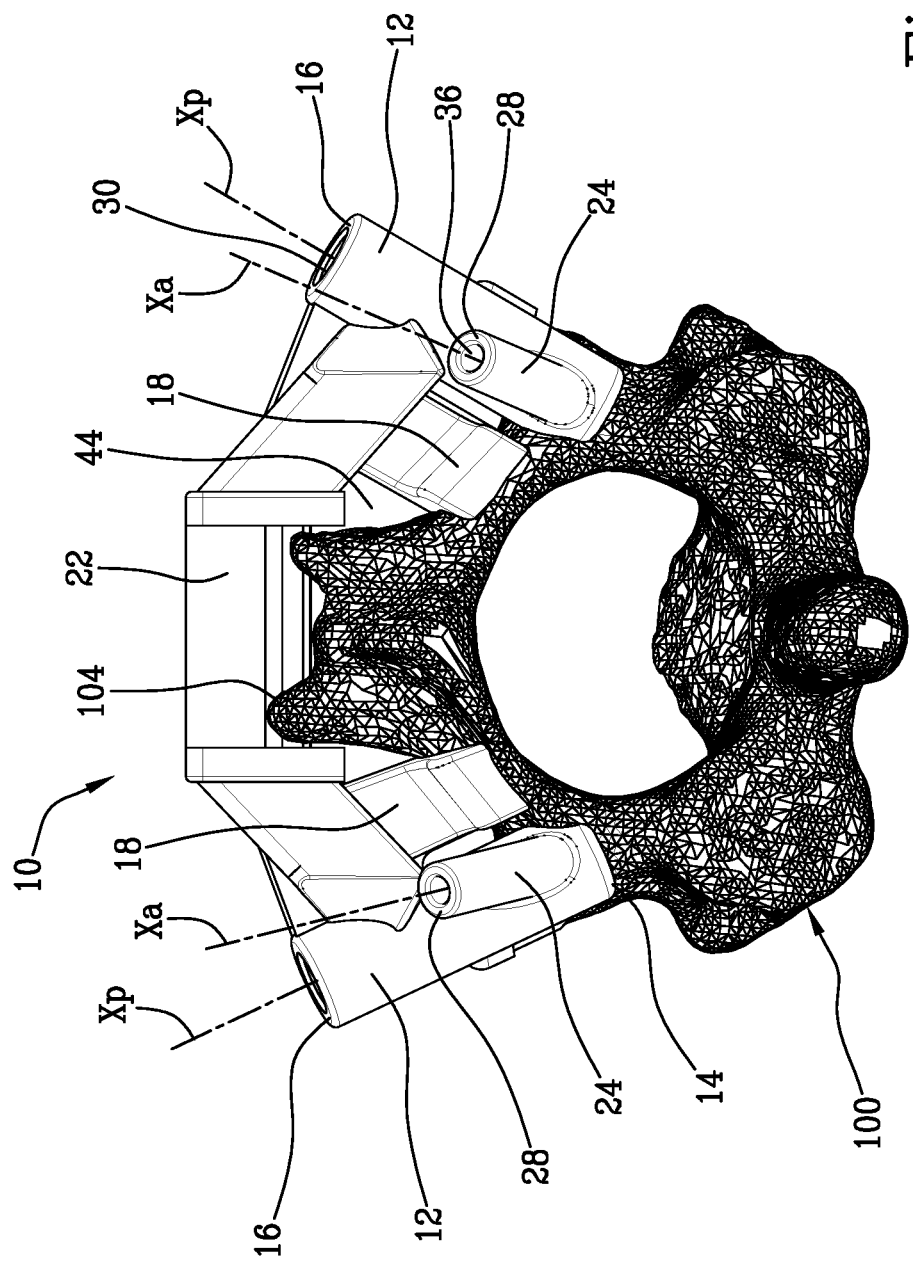
FIG. 6 is a perspective view of a disposable guide device according to a third embodiment of the invention correctly resting on the respective vertebra.
Figure 7:
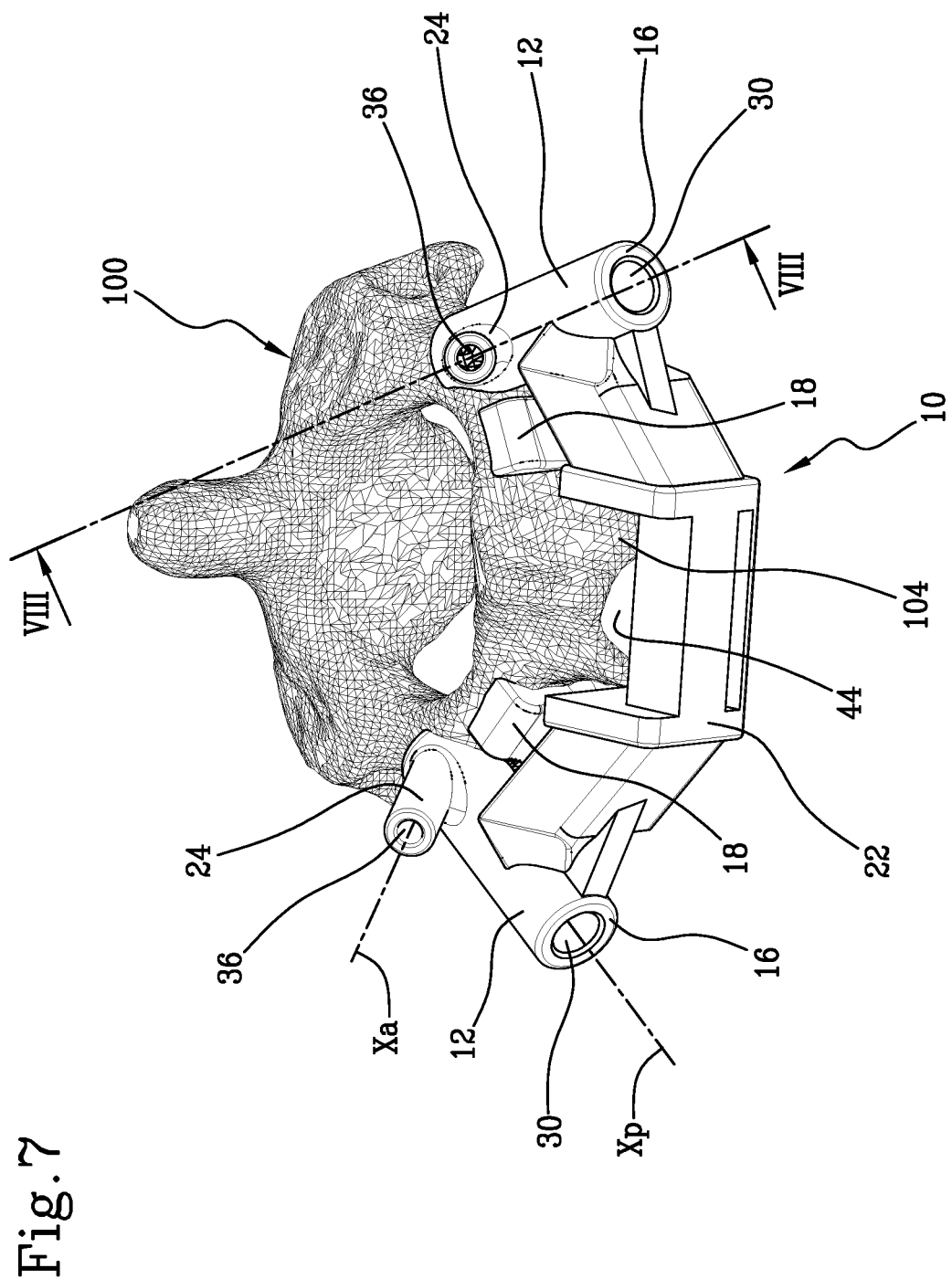
FIG. 7 shows a different view of the device of FIG. 6 correctly resting on the respective vertebra.

Alternatively, for example in the embodiment shown in FIGS. 6-7, the seat 44 for housing the spinous process 104 can be closed in the cranial-caudal direction by one or more partitions 46 connecting the sides of the junction element 22, respectively forming a semi-open or closed profile surrounding the spinous process 104, so as to ensure excellent stability to the guide device 10.

According to a further optional aspect of the present invention, the junction element 22 preferably comprises a handle 48 suitable to facilitate the surgeon's handling of the device 10. For instance, the handle 48 can extend from the junction element 22 (see, for example, figures from 2 to 4). Alternatively, the handle 48 can extend similarly to the junction element 22, joining the two guide sleeves 12 to each other.

In order to promote the stability of the device 10, it comprises a plurality of support elements 18 preferably arranged near the proximal end 14 of each guide sleeve 12. Each support element 18 defines a contact area 20 configured for abutting against a specific portion of the virtual surface 102 of the patient's vertebra 100, in a coupling configuration.

Preferably, this portion is one side of the spinous process 104, a lamina, an articular process, or a transverse process of the patient's vertebra 100. As already mentioned for the sleeves, the support elements 18, and in particular the respective contact areas 20, are also designed during the preoperative phase, by means of computer-aided design tools, on a three-dimensional model of the bone structure. This model is developed from a three-dimensional image obtained, for example, by computerized tomography and/or magnetic resonance of the patient's vertebra 100. Therefore, each contact area 20 of the support elements 18 is designed so that it uniquely matches the bone structure of the patient.

In some embodiments, at least one of the support elements 18 is shaped like a hook. In other words, this support element 18 comprises a contact area 20 which is shaped as a whole so as to at least partially encircle a portion of the vertebra 100 and to rest on the vertebra 100 from different directions. By way of example, in the embodiment in figures from 2 to 4, it can be seen that the two support elements 18 are both shaped like a hook, so that each one defines a contact area 20 designed to rest on the arch or lamina of the vertebra 100 partly in the cranial direction and partly in the caudal direction.

Advantageously, this allows a reduced, but particularly firm support area to be obtained.

In certain embodiments, each guide sleeve 12 is also provided with a further contact portion 50, also located near the proximal end 14 of the guide sleeve 12 and configured to abut against a portion of the virtual surface 102 of the vertebra 100. Preferably, this contact portion 50, just like the contact areas 20, is also shaped complementarily to the virtual surface of the respective portion of the patient's individual vertebra 100.

The invention achieves the intended objects and attains important advantages.

In fact, the presence of the auxiliary sleeves 24 allows the surgeon to incise the surface of the vertebra 100 by operating along a direction Xa which is more favourable than that of the guide sleeves 12.

Once the preparatory drill has made the surface incision, the insertion of the main surgical tool 42 is considerably simplified and therefore is not likely to undergo dangerous deviations.

It is clear that the specific features are described in relation to different embodiments of the invention for illustrative and non-limiting purposes. Obviously, a person skilled in the art can make further modifications and variations to the present invention in order to meet contingent and specific requirements. For instance, the technical features described in relation to one embodiment of the invention may be extrapolated from it and applied to other embodiments of the invention. Such modifications and variations also fall within the scope of protection of the invention as defined in the following claims.

The invention claimed is:

1. A disposable guide device for spinal surgery, comprising:
   two guide sleeves extending between a proximal end and a distal end for guiding a surgical intervention on a vertebra of a patient;
   a plurality of support elements, wherein each support element defines a contact area specifically configured for abutting against a portion of a virtual surface reproducing the vertebra of the patient, in a coupling configuration;
   at least one junction element joining the two guide sleeves together, wherein each guide sleeve comprises a respective auxiliary sleeve extending between a proximal end and a distal end the proximal end of the auxiliary sleeve is located in proximity to the proximal end of the respective guide sleeve.

2. The guide device according to claim 1, wherein each guide sleeve and the respective auxiliary sleeve have a diverging development starting from the respective proximal ends.

3. The guide device according to claim 1, wherein each guide sleeve extends along a respective main axis and wherein the respective auxiliary sleeve extends along a respective auxiliary axis.

4. The guide device according to claim 3, wherein each auxiliary axis intersects the respective main axis.

5. The guide device according to claim 3, wherein each auxiliary axis forms an angle with the respective main axis.

6. The guide device according to claim 5, wherein the angle is between 20° and 60°.

7. The guide device according to claim 3, wherein the auxiliary axis reaches a minimum distance from the main axis in proximity to the virtual surface of the vertebra.

8. The guide device according to claim 3, wherein the auxiliary axis reaches a minimum distance from the main axis or intersects the main axis, at a point inside the vertebra, within 5 mm from the virtual surface.

9. The guide device according to claim 3, wherein each auxiliary axis forms an angle with the portion of the virtual surface on which the auxiliary axis is incident, the angle being favourable to the use of a preparatory drill.

10. The guide device according to claim 9, wherein the angle is between 60° and 120.

11. The guide device according to claim 1, wherein the guide sleeves are oriented so that their proximal ends are further away from each other than the distal ends.

12. The guide device according to claim 1, wherein at least one of the support elements is shaped like a hook, so as to at least partially encircle a portion of the vertebra.

13. The guide device according to claim 1, further comprising a handle.

14. The guide device according to claim 6, wherein the angle is between 25° and 45°.

15. The guide device according to claim 10, wherein the angle is between 75° and 105°.

* * * * *